US009187704B2

(12) United States Patent
Inoue et al.

(10) Patent No.: US 9,187,704 B2
(45) Date of Patent: Nov. 17, 2015

(54) METHOD OF BIOMASS GASIFICATION

(76) Inventors: Hitoshi Inoue, Kunitachi (JP);
Masayuki Horio, Tokyo-To (JP)

(*) Notice: Subject to any disclaimer, the term of this patent is extended or adjusted under 35 U.S.C. 154(b) by 1077 days.

(21) Appl. No.: 10/485,608

(22) PCT Filed: Jul. 29, 2002

(86) PCT No.: PCT/JP02/07658
§ 371 (c)(1),
(2), (4) Date: Jan. 30, 2004

(87) PCT Pub. No.: WO03/012012
PCT Pub. Date: Feb. 13, 2003

(65) Prior Publication Data
US 2004/0180971 A1  Sep. 16, 2004

(30) Foreign Application Priority Data
Jul. 31, 2001  (JP) .................. 2001-231093

(51) Int. Cl.
*C10J 3/54* (2006.01)
*C07C 29/151* (2006.01)
*C10J 3/48* (2006.01)
*C10K 3/02* (2006.01)
*C10K 3/04* (2006.01)

(52) U.S. Cl.
CPC .............. *C10J 3/54* (2013.01); *C07C 29/1518* (2013.01); *C10J 3/482* (2013.01); *C10K 3/023* (2013.01); *C10K 3/04* (2013.01); *C10J 2300/0906* (2013.01); *C10J 2300/0916* (2013.01); *C10J 2300/0956* (2013.01); *C10J 2300/0973* (2013.01); *C10J 2300/0983* (2013.01); *C10J 2300/1659* (2013.01); *C10J 2300/1665* (2013.01); *Y02E 50/18* (2013.01); *Y02E 50/32* (2013.01); *Y02E 50/343* (2013.01)

(58) Field of Classification Search
CPC ................ C10J 2300/0916; C10J 2300/092
USPC ......... 585/240, 241, 242, 357, 408, 469, 638, 585/733; 48/197 FM; 71/903
See application file for complete search history.

(56) References Cited

U.S. PATENT DOCUMENTS 4,300,009 A * 11/1981 Haag et al. ................ 585/408
4,385,121 A *  5/1983 Knowlton .................. 435/244

FOREIGN PATENT DOCUMENTS

| CN | 1179462 A | * | 4/1998 |
| DE | 4409643 A1 | * | 9/1995 |
| DE | 4409643 A 1 | | 9/1995 |
| JP | 05-086374 | | 4/1993 |
| JP | 05-213778 | | 8/1993 |
| JP | 07-041767 | | 2/1995 |
| JP | 07041767 A | * | 2/1995 |
| JP | 07-138580 | | 5/1995 |
| JP | 09-111254 | | 4/1997 |

OTHER PUBLICATIONS

J. Arauzo et al., Catalytic Pyrogasification of Biomass—Evaluation of Modified Nickel Catalysts, 36 Ind. Eng. Chem. Res. 67-75 (1997).*
M.G.F. Rodrigues, Physical and Catalytic Characterization of Smectites From Boa-Vista, Paraiba, Brazil, 49 Ceramica 146-150 (2003).*
Arauzo et al., Catalytic Pyrogasification of Biomass—Evaluation of Modified Nickel Catalysts, 36 Ind. Eng. Chem. Res. 67-75 (1997).*
"Loess" in Brittanica Online Encyclopedia (2007), available at http://www.search.eb.com/eb/article-9048734.*
B.-M. Steenari and O. Lindqvist, High-Temperature Reactions of Straw Ash and the Anti-Sintering Additives Kaolin and Dolomite, 14 Biomass Bioenergy 67-76 (1998).*
M. Ohman and A. Nordin, The Role of Kaolin in Prevention of Bed Agglomeration During Fluidized Bed Combustion of Biomass Fuels, 14 Energy Fuels 618-624 (2000).*
Dr. IR H.A. Masson, entitled "A Twin Fluid Bed Pyrolyser Combustor System," Research in Thermochemical Biomass Conversion, 1988, pp. 725-743.

* cited by examiner

*Primary Examiner* — Randy Boyer
(74) *Attorney, Agent, or Firm* — The Webb Law Firm

(57) ABSTRACT

The present invention is directed to the provision of a method for efficiently producing a feedstock gas for use in the synthesis of liquid fuels including methanol by gasification of harbaceous plant or woody biomass feedstocks. Specifically, the present invention relates to a method for gasifying biomass to produce a feedstock gas for use in the production of liquid fuels including methanol, characterized by comprising the step of bringing a biomass-containing organic feedstock into fluid contact with a gasification accelerator comprising a clay having a catalytic function and/or a heating medium function in a gasification reaction zone under a raised temperature condition in the presence of a gasifying agent to convert the organic feedstock to gas useful for the production of a liquid fuel.

6 Claims, No Drawings

METHOD OF BIOMASS GASIFICATION

TECHNICAL FIELD

The present invention relates to a technique for converting biomass to a liquid fuel and more particularly to an efficient method for gasifying biomass to produce a feedstock gas for use in the production of liquid fuels such as methanol. The present invention also relates to the utilization, as a gaseous fuel, of useful gas produced by the gasification of biomass and the use, as a soil conditioner, of a waste catalyst and ash-containing waste as by-products produced by carrying out the gasification method.

BACKGROUND ART

In these days, the development of techniques for natural energy and the widespread use of these techniques are urgently needed for preventing global warming and for avoiding the depletion of limited fossil fuel resources. Among various types of natural energy, biomass energy is often regarded as the most promising natural energy from the viewpoint of its abundance and storability. Direct combustion of woody biomass which has hitherto been adopted, however, suffers from limited amount of resource and low efficiency, and, further, only electric power can be supplied by the direct combustion of woody biomass. On the other hand, in the production of ethanol by fermentation, only a limited part of biomass, for example, sugar such as sugarcane juice or molasses and starchy materials such as corn and potatoes can be used as the feedstock. The development of techniques, which can utilize the whole of biomass including cellulose and hemicellulose occupying a major part of photosynthetic products and can produce liquid fuels for engine or transportation applications, such as methanol, is of great significance. At the present time, however, such techniques are not in a practical stage for technical and economical reasons.

For example, Japanese Patent Laid-Open No. 138580/1995 describes an example of conventional techniques for gasifying organic matter such as biomass to obtain gas for use in the synthesis of methanol. This method includes partial oxidation of organic matter with air or oxygen and steam. In this case, the molar ratio of feed steam to carbon contained in the organic matter is regulated to 1 to 10, and the combustion or gasification temperature is regulated to 700 to 900° C. Japanese Patent Laid-Open No. 111254/1997 proposes a method wherein tar and soot, contained in gas produced by the above method, are decomposed in a gas decomposition furnace, into which a nickel-containing alloy or a nickel catalyst has been packed, provided on the downstream side of the gasification furnace.

On the other hand, Japanese Patent Laid-Open No. 41767/1995 proposes a method wherein biomass is decomposed within a vertical retort at 600 to 1200° C., generally 800 to 1100° C., in the presence of water.

According to the present inventor's finding, the above-described conventional methods respectively have the following problems to be solved.

(1) The Method in which Biomass is Partially Oxidized with Air or Oxygen and Steam In this method, tar is produced as a by-product at a reaction temperature of 700° C. or below. On the other hand, when the reaction temperature is 900° C. or above, soot is produced. The tar and soot reach the interior of the gasification furnace and heat recovery equipment and gas scrubbing equipment provided on the downstream side of the gasification furnace, and further reach even a shift reactor, $CO_2$ removing equipment, and methanol synthesizing equipment, resulting in blocking or lowered reaction yield. An attempt to maintain the temperature of the gasification furnace at 700° C. or above for avoiding this unfavorable phenomenon requires the combustion of a given part of the biomass. Consequently, the yield of the contemplated gas is lowered. Further, in this case, air or oxygen should be introduced into the gasification furnace for the combustion purposes. The use of air, however, results in dilution of the gas for methanol synthesis with nitrogen, and the use of oxygen requires the provision of a troublesome process for purifying pure oxygen from air. Therefore, this method is also disadvantageous in production cost.

(2) The Method in which a Gas Decomposition Furnace is Provided Downstream of the Gasification Furnace It is considered that, in the course of travel of the decomposition product from the gasification furnace to the gas decomposition furnace, a polymerization or condensation reaction of the decomposition product proceeds. Further, this method is also disadvantageous in thermal efficiency, because, when the gas produced in the gasification furnace is led to the gas decomposition furnace, heating should be newly carried out. Furthermore, since the catalyst used in the gas decomposition furnace is severely deteriorated, frequent replacement of the catalyst is necessary.

(3) Decomposition in the Presence of Water

In this method, treatment at a high temperature of about 1000° C. is necessary. Further, this method is considered unsuitable for continuous treatment. In Japanese Patent Laid-Open No. 41767/1995, there is no description on the composition of the produced gas. However, for some composition, the degree of reliance on composition adjustment in steam reforming, which is carried out on the downstream side, is so large that the yield of methanol is inevitably lowered.

SUMMARY OF THE INVENTION

In view of the above problems of the prior art, the present invention has been made. An object of the present invention is to provide a method which enables the gasification reaction of biomass to efficiently and effectively proceed under relatively low temperature conditions and, at the same time, can solve problems associated with the formation of tar and soot.

The above object of the present invention can be attained by a method for gasifying biomass to produce a feedstock gas for use in the production of liquid fuels including methanol, said method comprising the step of bringing a biomass-containing organic feedstock into fluid contact with a gasification accelerator comprising a clay having a catalytic function and/or a heating medium function in a gasification reaction zone under a raised temperature condition in the presence of a gasifying agent to convert the organic feedstock to gas useful for the production of a liquid fuel.

The method of the present invention may further comprise the step of withdrawing the gasification accelerator, on which by-products including char produced in the course of the gasification have been adsorbed, from the gasification reaction zone, introducing the withdrawn gasification accelerator into a regeneration zone, where the by-products adhered and adsorbed on the gasification accelerator is removed by combustion or by a carbonaceous material gasification reaction under a raised temperature condition provided by partial combustion, and recycling the regenerated gasification accelerator in a heated state into the gasification reaction zone.

The present invention also includes use of the useful gas produced by carrying out the above gasification method, as a gaseous fuel.

The present invention also includes a process for producing a liquid fuel, comprising the step of optionally subjecting the feedstock gas containing carbon monoxide and hydrogen produced by the above gasification method to gas composition adjustment in a shift reactor and removing carbon dioxide and then subjecting the feedstock gas to a methanol synthesis reaction to produce methanol.

The present invention also includes use of waste containing a waste catalyst and ash produced by carrying out the above gasification method, as a soil conditioner.

According to the method of the present invention, biomass can be efficiently gasified under a relatively mild temperature condition of about 400 to 750° C. as the raised temperature condition in the gasification reaction.

BEST MODE FOR CARRYING OUT THE INVENTION

The method for the gasification of biomass according to the present invention is a method for gasifying biomass to produce a feedstock gas for use in the production of liquid fuels such as methanol. The method includes the step of finely powdering a biomass-containing organic feedstock and bringing the finely powdered biomass-containing organic feedstock into fluid contact with a solid gasification accelerator having a catalytic function and/or a heating medium function in a gasification reaction zone under a raised temperature condition in the presence of a gasifying agent to convert the finely powdered biomass feedstock to gas useful for the production of a liquid fuel.

The method of the present invention may further comprise the step of withdrawing the gasification accelerator, on which by-products such as char produced in the course of the gasification have been adsorbed, from the gasification reaction zone, introducing the withdrawn gasification accelerator into a regeneration zone, where the by-products adhered and adsorbed on the gasification accelerator is removed by combustion or by a carbonaceous material gasification reaction under a raised temperature condition provided by partial combustion, and recycling the regenerated gasification accelerator in a heated state into the gasification reaction zone. The adoption of the gasification accelerator regeneration-recycle step can further improve the efficiency of the gasification of biomass.

Biomass feedstocks to which the method of the present invention can be applied are not particularly limited and include all useful organic materials from which useful liquid fuel components such as methanol can be produced. Specific examples of biomass feedstocks usable herein include: wood- or forest-derived woody materials; plant/algae resources derived from marshes, rivers, grasslands, and seas; forestry and agricultural product wastes; and waste plastics.

The fine grinding (powdering) or size reduction of these biomass-containing organic feedstocks is important for increasing the contact area (specific surface area) at the time of the gasification reaction to effectively and efficiently carry out the reaction. In this case, the feedstocks are finely ground or size reduced to a suitable size of about 300 to 3000 μm, preferably about 300 to 600 μm.

In the present invention, the organic feedstock is brought into fluid contact with a gasification accelerator comprising a clay having a catalytic function and/or a heating medium function in a gasification reaction zone under a raised temperature condition in the presence of a gasifying agent. The gasification of the biomass possibly proceeds in the presence of steam and air according to the following reaction.

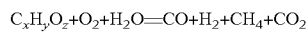

$$C_xH_yO_z+O_2+H_2O = CO+H_2+CH_4+CO_2$$

Therefore, oxygen and water are indispensable as reaction components for the gasification reaction. In the present invention, a mixture of heated steam with air may be used as the gasifying agent which is a component necessary for the gasification. The use of steam only is more preferred from the viewpoint of preventing a lowering in produced gas concentration. Steam is particularly preferred because of its function of fluidizing the catalyst and of stripping an oil on the catalyst. Further, as described below, the introduction of air into the regeneration zone can realize the removal of by-products adsorbed on the clay catalyst by combustion or by a combination of partial combustion with a carbonaceous material gasification reaction.

Regarding the amount and temperature condition of the gasifying agent introduced into the gasification reaction zone, respective optimal ranges can be properly selected depending upon the type, amount, and properties of the biomass feedstock to be reacted. The amount of steam introduced as the gasifying agent is generally in the range of from 0.3 to 2.5, preferably in the range of from 0.5 to 1.0, in terms of steam/biomass ratio. The temperature conditions for the gasification reaction will be described later in detail.

The steam is preferably introduced so that the powder is fluidized. This fluidization can realize fluid catalytic gasification by virtue of good contact among steam, polymers and heat decomposition products of biomass liberated in the gas phase, and catalyst particles in the gasification reaction zone.

The gasification accelerator to be brought into fluid contact with the biomass feedstock in the gasification reaction comprises a clay having a catalytic function and/or a heating medium function, and an optimal gasification accelerator can be selected by taking into consideration the type of biomass, the design of equipment provided downstream of the gasification reaction zone, and the cost of the whole process. Specifically, the gasification accelerator preferably comprises at least one member selected from the group consisting of smectite clay, vermiculite clay, kaolin-serpentine clay, chlorite clay, and mixtures thereof, more preferably at least one member selected from the group consisting of smectite clay, vermiculite clay, kaolinite clay, halloysite clay, and mixtures thereof.

In the gasification accelerator comprising clay as an indispensable component, if necessary, at least one member selected from the group consisting of other minerals, diatomaceous earth, shells, silica alumina catalysts, transition metal-supported inorganic material catalysts, metal oxide catalysts, and mixtures thereof may be additionally added.

The particle diameter of the gasification accelerator is preferably about 10 to 500 μm, more preferably 60 to 120 μm.

Regarding the amount of the gasification accelerator introduced, an optimal amount range can be properly selected depending upon the type and properties of the gasification accelerator and biomass feedstock used and the equipment used.

In the conventional method for producing, from a biomass feedstock, a useful gas for the synthesis of methanol, studies using a catalyst in a gasification furnace have revealed that, in this method, the catalyst is deteriorated in an earlier stage than expected. Consequently, at the present time, the conventional method has not been put to practical use. Further, as described above, the most serious problem involved in producing a useful gas from the biomass feedstock is the formation of tar or soot. When the gasification reaction furnace is operated at a relatively low temperature of 700° C. or below, the formation of tar is unavoidable. On the other hand, at a high temperature of 900° C. or above, soot is formed, and, in addition, it becomes difficult to maintain self-reliant heat balance of the process.

The present inventor has found that, in the gasification reaction, bringing the biomass feedstock into fluid contact with the gasification accelerator comprising clay can solve the above difficult problems at all once, which has led to the completion of the present invention.

In general, tar occurs when a polymer, which has been liberated from the biomass as a solid phase into a gas phase, remains undecomposed, or when a heat decomposition product having an unsaturated bond has undergone condensation or polymerization. It is considered that, for example, the presence of a metal catalyst having an affinity for a hydrogen atom or a proton-donating acid catalyst can cause rapid decomposition of this liberated component or the suppression of the polymerization of the liberated component. Thus, in the present invention, when the finely powdered gasification accelerator and the finely powdered biomass are brought into contact with each other in a fluidized state to allow the gasification reaction to proceed, the formation of tar in the gas phase can be effectively prevented and, in addition, the necessary temperature of the reaction zone can be significantly lowered. Therefore, according to this method, the yield of the produced gas and the heat balance of the process can be markedly improved. Further, the introduction of the gasification accelerator into the reaction system is also important from the viewpoint of allowing the gasification reaction to efficiently proceed through the action of the gasification accelerator as a heating medium.

Therefore, in the present invention, a clay component (optionally subjected to pretreatment), such as smectite clay, which is very easily available and is inexpensive, is used as a gasification accelerator and the gasification reaction can be carried out while continuously regenerating the gasification accelerator in the regeneration zone. According to this method, continuous replacement of a part of the gasification accelerator in a relatively high replacement ratio and, in addition, the removal of carbon, deposited on the gasification accelerator by the decomposition reaction, in the regeneration zone enables the catalytic decomposition reaction to be efficiently carried out while maintaining the catalytic activity of the gasification accelerator.

Accordingly, the gasification method according to the present invention can take two embodiments which are roughly classified according to the selection of reaction conditions in the reaction zone.

One of the embodiments is that a reaction vessel constituting a gasification reaction zone is operated in a relatively high temperature range of about 500 to 800° C. to avoid the deposition of carbon on the gasification accelerator. According to this embodiment, the provision of the regeneration zone of the gasification accelerator is not always required. The reaction zone may comprise means for supplying a finely powdered biomass feedstock, means for supplying a gasifying agent such as steam, and separation means for removing the finely powdered gasification accelerator and ash from the produced gas.

The other embodiment, which is a more preferred embodiment, is that the reaction is carried out in a lower temperature range of about 450 to 750° C. This embodiment comprises the step of depositing a carbonaceous component on the gasification accelerator and removing the carbonaceous component in a regeneration zone provided separated from the reaction zone by combustion or by a combination of partial combustion with a carbonaceous material gasification reaction. For example, a regeneration tower for regenerating the gasification accelerator comprises an air supply device and a device for separating the catalyst from the combustion exhaust gas. The reaction vessel is connected to the regeneration tower through piping so that the catalyst can be circulated through both the reaction vessel and the regeneration tower. In this case, the gasification reaction takes place in the reaction vessel, as well as in the piping upstream of the reaction vessel. At that time, tar is produced, and the produced tar is further polycondensed. As a result, the polycondensate is deposited as a carbon component (char) on the catalyst. The catalyst with the char deposited thereon is led to the regeneration tower. In the regeneration tower, air is supplied, and the deposited carbon component is entirely burned or partially burned. The heat of combustion heats the gasification accelerator. The heated gasification accelerator can be again circulated into the reaction vessel to supply necessary heat to the reaction.

In the conventional technique, when oxygen is supplied for carrying out the partial oxidation, separation and purification of oxygen from air are necessary. On the other hand, when air is supplied, gas for synthesizing methanol is disadvantageously diluted with nitrogen. By contrast, according to the method of the present invention, since air is used for combustion, the separation of oxygen is not necessary. This air is supplied to the regeneration tower, and waste gas is discharged as a stream in a system different from the produced gas discharged from the reaction vessel. Therefore, there is no fear of the gas for methanol synthesis being diluted with nitrogen.

The produced gas thus obtained is a feedstock gas suitable for methanol synthesis, which gas contains neither tar nor soot, is clean, and has a hydrogen to carbon monoxide ratio of about 2:1.

In a preferred embodiment of the present invention, the step of recovering at least a part of generated heat and/or at least a part of waste heat in the regeneration zone and effectively utilizing the recovered heat is further provided. The recovered heat can be effectively utilized, for example, for drying and heating of the biomass feedstock and the generation of steam as the gasifying agent.

Thus, in the present invention, the gasification accelerator is advantageous in that polymers and heat decomposition products of the biomass liberated in the gas phase can be rapidly decomposed by effectively bringing the solid gasification accelerator, which has been finely powdered, into fluid contact. In addition, it is considered that, by virtue of heat conduction as a result of contact between the biomass and the gasification accelerator and radiation from the gasification accelerator, the gasification accelerator plays an important role also as a heat transfer medium for transferring energy, necessary for the reaction, to the biomass. Further, when the operation is carried out at a relatively low temperature, the gasification accelerator is advantageous in that char as a by-product is adsorbed on the surface of the catalyst, and heat generated by combustion of the adsorbed char in the regeneration tower is transferred to the reaction zone to heat the biomass. These various functions of the gasification accelerator can markedly improve the heat balance of the gasification reaction process and can realize the production of a gas for methanol synthesis under mild temperature and pressure conditions with high efficiency.

The present invention includes a process for producing a liquid fuel, such as methanol, from a useful feedstock gas produced by the above method. Specifically, if necessary, the gas produced in the above process is subjected to gas composition adjustment in a shift reactor, and carbon dioxide is removed in a carbon dioxide removing device. The gas can be then subjected to a catalytic reaction in a methanol synthesis apparatus to produce methanol. Therefore, the process for producing methanol from the produced gas can be properly carried out by conventional means.

Further, in the present invention, since the gasification accelerator used comprises clay, a mixture of waste catalyst (clay) with ash to be disposed of after the reaction as such can be returned to soil, for effective utilization as a soil conditioner. In particular, when continuously harvesting biomass leads to a fear of the fertility/productivity of soil being gradually deteriorated, the utilization of the soil conditioner is useful. The utilization of the waste as a soil conditioner can advantageously improve acid soil and can supply the soil with a mineral component. Further, when the soil to which the waste is returned has certain properties, an improvement in nutriment absorption and water retention by the clay can enhance the productivity of the soil.

Furthermore, according to the present invention, the useful gas produced by carrying out the above gasification method as such can be used as a gaseous fuel.

EXAMPLES

Example 1

A stainless steel reaction vessel having an inner diameter of 43 mm and a height of 500 mm was packed with any one of activated clay and quartz sand as a bed material. While fluidizing the bed material by nitrogen gas and steam, cellulose powder was introduced into the reactor from its top to gasify the cellulose powder. The activated clay was such that, after addition of water, the clay was granulated to prepare granules, the granules were dried and then fired at 600 to 650° C., and the fired clay was sieved to recover a size fraction of 74 to 125 μm in particle diameter which was then used as the bed material. The quartz sand used had a particle diameter of 250 to 300 μm. Main reaction conditions and experimental results were as follows.

As can be seen from the results shown in Table 1, as compared with the use of quartz sand having no catalytic action, the use of a clay catalyst such as activated clay can markedly suppress the formation of tar and thus can contribute to enhanced yield of gas. In these experiments, the produced gas had a hydrogen concentration of 15 to 20% and a carbon monoxide concentration of 50 to 55%. From the viewpoint of the synthesis of methanol in the subsequent state, the produced gas is preferably a hydrogen-rich gas produced as a result of further progress of a shift reaction ($CO + H_2O = CO_2 + H_2$). Studies by J. CORELLA et al. (J. CORELLA, J. HERGUIDO, F. J. ALDAY "PYROLYSIS AND STEAM GASIFICATION OF BIOMASS IN FLUIDIZED BEDS: INFLUENCE OF THE TYPE AND LOCATION OF THE BIOMASS FEEDING POINT ON THE PRODUCT DISTRIBUTION" International Conference on Research in Thermochemical Biomass Conversion, Phenix, Ariz. pp 384-398 (1988)) show that, as compared with the reactor used in this example wherein the biomass is introduced from the top of the reactor, the introduction of the biomass directly into the bottom of the reactor with the bed material being packed thereinto can markedly enhance the concentration of hydrogen in the produced gas (at 650° C., in the case of the introduction of the biomass from the top of the reactor, the hydrogen concentration is 20%, while in the case of the introduction of the biomass from the bottom of the reactor, the hydrogen concentration is about 47%).

Example 2

The same reaction vessel as used in Example 1 was packed with activated clay, which had been once used as a gasification accelerator and then regenerated, as a bed material. In the same manner as in Example 1, while fluidizing the bed material by nitrogen gas and steam, cellulose powder was introduced into the reactor from its top. In the regeneration of the activated clay, the used activated clay was heated at 850° C. for 60 min to completely remove char adsorbed on the activated clay, and the heated clay was then sieved to recover a size fraction of 74 to 125 μm in particle diameter which was then used as the bed material. Main experimental conditions and results were as follows.

TABLE 1

|  | Experiment No. | | | |
| --- | --- | --- | --- | --- |
|  | 1 | 2 | 3 | 4 |
| Bed material | Activated clay | Quartz sand | Activated clay | Quartz sand |
| Reaction temp. | 650° C. | 650° C. | 550° C. | 550° C. |
| Reaction pressure | Atmospheric pressure | Atmospheric pressure | Atmospheric pressure | Atmospheric pressure |
| Amount of bed material, g | 98.0 | 152.3 | 80.5 | 150.4 |
| Fluidizing gas | Nitrogen/steam | Nitrogen/steam | Nitrogen/steam | Nitrogen/steam |
| Amount of cellulose introduced, g | 1.04 | 1.08 | 1.05 | 0.99 |
| Steam/cellulose ratio | 2.07 | 1.78 | 1.87 | 1.98 |
| Uo-Umf, m/s | 0.08 | 0.08 | 0.08 | 0.08 |
| Carbon conversion |  |  |  |  |
| Gas, % | 65.0 | 47.5 | 51.2 | 32.5 |
| Tar, % | 1.5 | 25.6 | 1.8 | 38.3 |
| Char, % | 33.0 | 22.3 | 42.6 | 27.5 |
| Total, % | 99.5 | 95.4 | 95.6 | 98.3 |

TABLE 2

| | Experiment No. | | | |
|---|---|---|---|---|
| | 1 | 5 | 3 | 6 |
| Bed material | Activated clay | Regenerated activated clay | Activated clay | Regenerated activated clay |
| Reaction temp. | 650° C. | 650° C. | 550° C. | 550° C. |
| Reaction pressure | Atmospheric pressure | Atmospheric pressure | Atmospheric pressure | Atmospheric pressure |
| Amount of bed material, g | 98.0 | 95.5 | 80.5 | 82.3 |
| Fluidizing gas | Nitrogen/steam | Nitrogen/steam | Nitrogen/steam | Nitrogen/steam |
| Amount of cellulose introduced, g | 1.04 | 1.02 | 1.05 | 1.03 |
| Steam/cellulose ratio | 2.07 | 1.96 | 1.87 | 2.05 |
| Uo-Umf, m/s | 0.08 | 0.08 | 0.08 | 0.08 |
| Carbon conversion | | | | |
| Gas, % | 65.0 | 61.6 | 51.2 | 49.5 |
| Tar, % | 1.5 | 1.7 | 1.8 | 2.2 |
| Char, % | 33.0 | 35.2 | 42.6 | 44.8 |
| Total, % | 99.5 | 98.5 | 95.6 | 96.5 |

In Table 2, the main reaction conditions and experimental results of Experiment Nos. 1 and 3 in Table 1 were again described for comparison of the use of fresh activated clay with the use of the regenerated activated clay. The results in Table 2 show that, advantageously, activated clay even after regeneration can significantly suppress the formation of tar.

According to the method of the present invention, in gasifying a biomass feedstock to produce a feedstock gas for use in the production of liquid fuels such as methanol, clay is used as a gasification accelerator in the gasification reaction zone. This constitution enables the gasification reaction of the biomass to efficiently and effectively proceed under relatively low temperature conditions and, at the same time, can solve problems associated with the formation of tar and soot.

Further, according to the present invention, useful gas produced by the gasification of biomass can be utilized as a gaseous fuel. In addition, a waste catalyst and ash-containing waste as by-products produced by carrying out the gasification method can be effectively utilized as a soil conditioner. Thus, the present invention is very useful as an industrial technique suitable for a recycle type society.

The invention claimed is:

1. A method for gasifying a biomass to produce a useful gas, the biomass comprising a material selected from the group consisting essentially of wood- or forest-derived woody materials, plant/algae resources, and forestry/agricultural product wastes, said method comprising the steps of:

introducing the biomass and a gasifying agent separately from each other into a gasification reaction zone, the gasifying agent comprising steam;

bringing the biomass into contact with a gasification accelerator in a fluidized state, the gasification accelerator having a catalytic function for a biomass gasifying reaction and a heating medium function in the gasification reaction zone under a raised temperature condition in the presence of the gasifying agent to convert the biomass to a useful gas containing carbon monoxide and hydrogen, said gasification accelerator having an average particle diameter of 60 to 500 microns and comprising smectite clay; and withdrawing the gasification accelerator, on which by-products including char produced in the course of the gasification have been adsorbed, from the gasification reaction zone, introducing the withdrawn gasification accelerator into a regeneration zone, where the by-products adhered and adsorbed on the gasification accelerator are removed by combustion or by a combination of partial combustion with a carbonaceous material gasification reaction, and recycling the regenerated gasification accelerator in a heated state into the gasification reaction zone.

2. A method for gasifying a biomass to produce a useful gas, the biomass comprising a material selected from the group consisting essentially of wood- or forest-derived woody materials, plant/algae resources, and forestry/agricultural product wastes, said method comprising the steps of:

introducing the biomass and a gasifying agent separately from each other into a gasification reaction zone, the gasifying agent comprising steam;

bringing the biomass into contact with a gasification accelerator in a fluidized state, the gasification accelerator having a catalytic function for a biomass gasifying reaction and a heating medium function in the gasification reaction zone under a raised temperature condition in the presence of the gasifying agent to convert the biomass to a useful gas containing carbon monoxide and hydrogen, said gasification accelerator having an average particle diameter of 60 to 500 microns and comprising smectite clay, wherein the raised temperature condition is in the range of 400 to 800° C.

3. The method according to claim 1, which further comprises the step of recovering at least a part of generated heat and/or at least a part of waste heat in the regeneration zone and effectively utilizing the recovered heat.

4. A method for producing a liquid fuel, comprising the step of optionally subjecting feedstock gas containing carbon monoxide and hydrogen to gas composition adjustment in a shift reactor and removing carbon dioxide and then subjecting the feedstock gas to a methanol synthesis reaction to produce methanol, the feedstock gas produced by a method for gasifying a biomass, the biomass comprising a material selected from the group consisting essentially of wood- or forest-derived woody materials, plant/algae resources, and forestry/agricultural product wastes, the method comprising the steps of:

introducing the biomass and a gasifying, agent separately from each other into a gasification reaction zone, the gasifying agent comprising steam;

bringing the biomass into contact with a gasification accelerator in a fluidized state, the gasification accelerator having a catalytic function for a biomass gasifying reaction and a heating medium function in the gasification reaction zone under a raised temperature condition in the presence of the gasifying agent to convert the biomass to a useful gas containing carbon monoxide and hydrogen, said gasification accelerator having an average particle diameter of 60 to 500 microns and comprising at least one member selected from the group consisting of smectite clay.

5. The method according to claim 2, wherein the temperature condition is in the range of 400 to 750° C.

6. The method according to claim 2, wherein the temperature condition is in the range of 450 to 600° C.

* * * * *